(12) United States Patent
Passananti et al.

(10) Patent No.: US 8,304,235 B2
(45) Date of Patent: Nov. 6, 2012

(54) NUCLEIC ACID CODIFYING FOR A UTROPHIN TRANSCRIPTION SPECIFIC REGULATING PROTEIN, PROTEIN CODIFIED THEREBY AND USES THEREOF

(75) Inventors: Claudio Passananti, Rome (IT); Nicoletta Corbi, Rome (IT); Annalisa Onori, Rome (IT); Maria Grazia Di Certo, Rome (IT)

(73) Assignee: CNR- Consiglio Nazionale Delle Ricerche, Rome (IT)

( * ) Notice: Subject to any disclaimer, the term of this patent is extended or adjusted under 35 U.S.C. 154(b) by 289 days.

(21) Appl. No.: 12/680,681

(22) PCT Filed: Oct. 6, 2008

(86) PCT No.: PCT/IB2008/054089
§ 371 (c)(1),
(2), (4) Date: Mar. 29, 2010

(87) PCT Pub. No.: WO2009/044383
PCT Pub. Date: Apr. 9, 2009

(65) Prior Publication Data
US 2010/0216712 A1    Aug. 26, 2010

(30) Foreign Application Priority Data
Oct. 5, 2007   (IT) .............................. RM2007A0523

(51) Int. Cl.
*C12N 15/00* (2006.01)
*C07H 21/02* (2006.01)
*C07K 14/00* (2006.01)

(52) U.S. Cl. ..................... 435/320.1; 536/23.1; 530/350
(58) Field of Classification Search ................. 530/350; 536/23.1; 435/320.1
See application file for complete search history.

(56) References Cited

U.S. PATENT DOCUMENTS
6,242,568 B1 * 6/2001 Barbas et al. .................. 530/350

OTHER PUBLICATIONS

Onori, et al., "The artificial 1,10-12, 4-zinc-finger protein Bagly binds human 17-21 utrophin promoter A at the endogenous chromosomal site and activates transcription.", Biochemistry and Cell Biology, 85(3):358-365, 2007.
Beltran, et al., "Interrogating genomes with combinatorial artificial transcription factor libraries: asking zinc finger questions.", Assay and Drug Development Technologies, 4(3):317-331, 2006.
Corbi, et al., "The artificial zinc finger coding gene jazz binds the utrophin promoter and activates transcription.", Gene Therapy, 7(12):1076-1083, 2000.
Segal, et al., "Evaluation of a modular strategy for the construction of novel polydactyl zinc finger DNA-binding proteins.", Biochemistry, 42(7):2137-2148, 2003.

* cited by examiner

*Primary Examiner* — Karen Cochrane Carlson
(74) *Attorney, Agent, or Firm* — Lucas & Mercanti, LLP (57) ABSTRACT

The present invention relates to a nucleic acid molecule comprising a nucleotide sequence codifying for a protein characterized in having at least four zinc finger domains and in modulating the transcription of the utrophin gene by binding to a nucleotidic sequence comprised in a utrophin gene untranscribed regulatory sequence. Protein codified thereby and uses thereof.

14 Claims, 2 Drawing Sheets

B "UtroUp" zinc finger domains

ILDRPYACPVESCDRRFSRSDNLVRHIRIHTG
SEQ ID 1
QKPFQCRICMRNFSRSDHLTTHNRTHTGEKPF
SEQ ID 2
ACDICGRKFADPGHLVRHNRIHTGEKPFACPV
SEQ ID 3
ESCDRRFSRSDELTRHIRIHTGQKPFQCRICM
SEQ ID 4
RNFSSRDVLRPHNRTHTGEKPFACDICGRKFA
SEQ ID 5
SRDVLRRHNRIHLRQNDLE
SEQ ID 6

NUCLEIC ACID CODIFYING FOR A UTROPHIN TRANSCRIPTION SPECIFIC REGULATING PROTEIN, PROTEIN CODIFIED THEREBY AND USES THEREOF

CROSS-REFERENCE TO RELATED APPLICATIONS

This application is a 371 of PCT/IB2008/054089 filed Oct. 6, 2008, which claims the benefit of Italian Application No. RM2007A000523 filed Oct. 5, 2007, the contents of each of which are incorporated herein by reference.

TECHNICAL FIELD OF THE INVENTION

The present invention relates to a nucleic acid comprising a nucleotidic sequence codifying for a protein regulating the utrophin transcription, called "UtroUp". UtroUp is able to bind, with very high affinity and specificity, a DNA target sequence of 18-nucleotide-long existing both in the human and murine promoter of "utrophin" gene and to modulate the transcription thereof.

STATE OF ART

Mutations in the dystrophin gene are responsible for myopathies linked to chromosome X, called Duchenne (DMD) and Becker (BMD) muscular dystrophies. The phenotype DMD is characterized by the complete absence of dystrophin, due to promoter defects or to mutations of nonsense type or deletions. DMD affects 1 out of 3500 borne males and it involves a progressive muscular weakening with lethal results. The phenotype BMD is less serious and more variable, as it is associated to a lowering of the expression levels of dystrophin mutated versions.

The dystrophin gene extends for about 2.5 megabases of DNA, in the Xp21 locus, with a corresponding transcript of 14 kilobases (accession number BC127103) and a protein of 427 kilodalton (accession number AA127104) (Davies et al. 1983). In 1989, an autosomal homologous of the dystrophin gene was described for the first time (Love et al., 1989). Such protein, at first defined DRP (dystrophin related protein), was subsequently called utrophin. The utrophin gene maps in chromosome 6q24, it has a transcript of 13 kilobases (accession number NM_007124) and a protein product of 400 kilodalton (accession number NP_009055). Utrophin and dystrophin have strong structural and functional homologies: both act like a connection bridge between the actin cytoskeleton, the cell membrane and, at last, the extracell matrix by means of the proteins collectively designated as DAPs (dystrophin associated proteins) (Matsumura et al. 1992). In adult muscle, utrophin is localized in the neuromuscular junction, whereas dystrophin is placed along the whole sarcolemma. Studies on "mdx" mice (murine model of DMD), transgenic for the utrophin have demonstrated that an over-expression and relocalization of utrophin induces a clear improvement of the dystrophic phenotype (Tinsley et al 1996, Rafael et al 1998). The increase in the utrophin expression levels is then currently one of the most promising therapeutic approaches for the DMD (Miura and Jasmin 2006) treatment. To this purpose, various pharmacological treatments have been proposed (Khurana and Davies 2003, Bogdanovich et al. 2004, Voisin and La Porte 2004).

The authors, in order to obtain utrophin over-expression have designed different synthetic zinc-finger based transcriptional factors able to bind and activate the utrophin gene transcription (Corbi et al. 2000, Corbi et al. 2004, Onori et al. 2007, Mattei et al. 2007). The affinity and specificity of binding to DNA is one of the critical points in the construction of synthetic zinc fingers. In a cellular context, a hypothetical transcriptional factor will recognize multiple DNA sequences with a different affinity level, by thus exerting an additional transcrictional regulation level. For natural transcriptional factors, the capability of recognizing specifically a determined target sequence has been accurately selected during the evolution, so that each regulating protein acts in the suitable pathway. Statistically, by assuming a stochastic distribution of the DNA bases, a 9-base long DNA sequence is present in the human genome ($\cong 3.5 \times 10^9$ bp) about $1.3 \times 10^4$ times, a 12-base long sequence about 210 times, whereas a 16-base sequence is present one time only.

In the present invention a new domain binding to DNA on zing finger base, called "UtroUp", has been synthesized and assayed. UtroUp has six zinc finger domains and it is able to bind, with very high affinity and specificity, a 18-nucleotide long target DNA sequence existing both in the human and murine promoter of the "utrophin" gene.

The aim is to make available synthetic transcriptional factors having an action targeted at the exclusive utrophin over-regulation.

SUMMARY OF THE INVENTION

Therefore the object of the present invention is a nucleic acid molecule comprising a nucleotide sequence codifying for a protein characterized in having at least four zinc finger domains and in modulating the transcription of the utrophin gene by binding to a nucleotidic sequence comprised in a utrophin gene untranscribed regulatory sequence. Preferably, the protein comprises six zinc finger domains.

Still preferably, the zinc finger domains are selected among: SEQ ID NO. 1, SEQ ID NO. 2, SEQ ID NO. 3, SEQ ID NO. 4, SEQ ID NO. 5 or SEQ ID NO. 6 and may also be present in more than one sequence copy.

More preferably the zinc finger domains are SEQ ID NO. 1, SEQ ID NO. 2, SEQ ID NO. 3, SEQ ID NO. 4, SEQ ID NO. 5 and SEQ ID NO. 6.

Yet preferably the nucleic acid molecule of the invention codifies for a protein comprising the SEQ ID NO. 12. Still preferably it codifies for a protein having the SEQ ID NO. 12. Preferably the nucleic acid molecule of the invention has essentially the SEQ ID NO. 11.

Still preferably the nucleic acid molecule of the invention codifies for a protein having essentially the SEQ ID NO. 8 or SEQ ID NO. 10. Preferably the nucleic acid molecule has essentially the SEQ ID NO. 7 or SEQ ID NO. 9, respectively.

It is a further object of the invention an expression vector comprising the nucleic acid molecule as described above.

It is a further object of the invention a recombinant host cell comprising the vector of the invention.

It is a further object of the invention a protein characterized in having at least four zinc finger domains and in modulating the transcription of the utrophin gene by binding to a nucleotidic sequence comprised in a utrophin gene untranscribed regulatory sequence. Preferably, the protein has six zinc finger domains. Preferably the nucleotidic sequence has essentially the sequence: GCT GCT GCG GGC TGG GAG (SEQ ID NO. 13).

Still preferably, the protein has essentially the SEQ ID NO. 12. More preferably, the protein has essentially the SEQ ID NO. 8 or SEQ ID NO. 10.

It is an objet of the invention the protein as described above for medical use. Preferably for use as an anti-muscular pathology agent.

It is an objet of the invention the expression vector as described above for gene therapy.

It is an objet of the invention the use of the protein as described above for the preparation of a medicament for a muscular pathology. Preferably, the muscular pathology is the Duchenne (DMD) or the Becker (BMD) muscular dystrophy.

In the present invention zinc-finger based domain is defined as a synthetic aminoacidic domain able to bind specifically a DNA sequence inside the utrophin gene promoter.

The present invention will be now described by non-limiting examples thereof, with particular reference to the following figures.

B) Histogram related to the luciferase activity of the pXP constructs (containing a small portion of the utrophin promoter including the UtroUp bond site) and pGL2-Control. Both constructs have been cotransfected with UtroUp, containing only the DNA binding domain, or V-UtroUp containing the DNA binding domain fused to the activation domain of the Vp16 transcription. The results represent the average of four independent experiments performed three times and are reported with respect to the basal activity (thereto the value 1 has been given) respectively of the pXP and pGL2-Control constructs.

MATERIALS AND METHODS

Sequences' Construction

Figure 1:
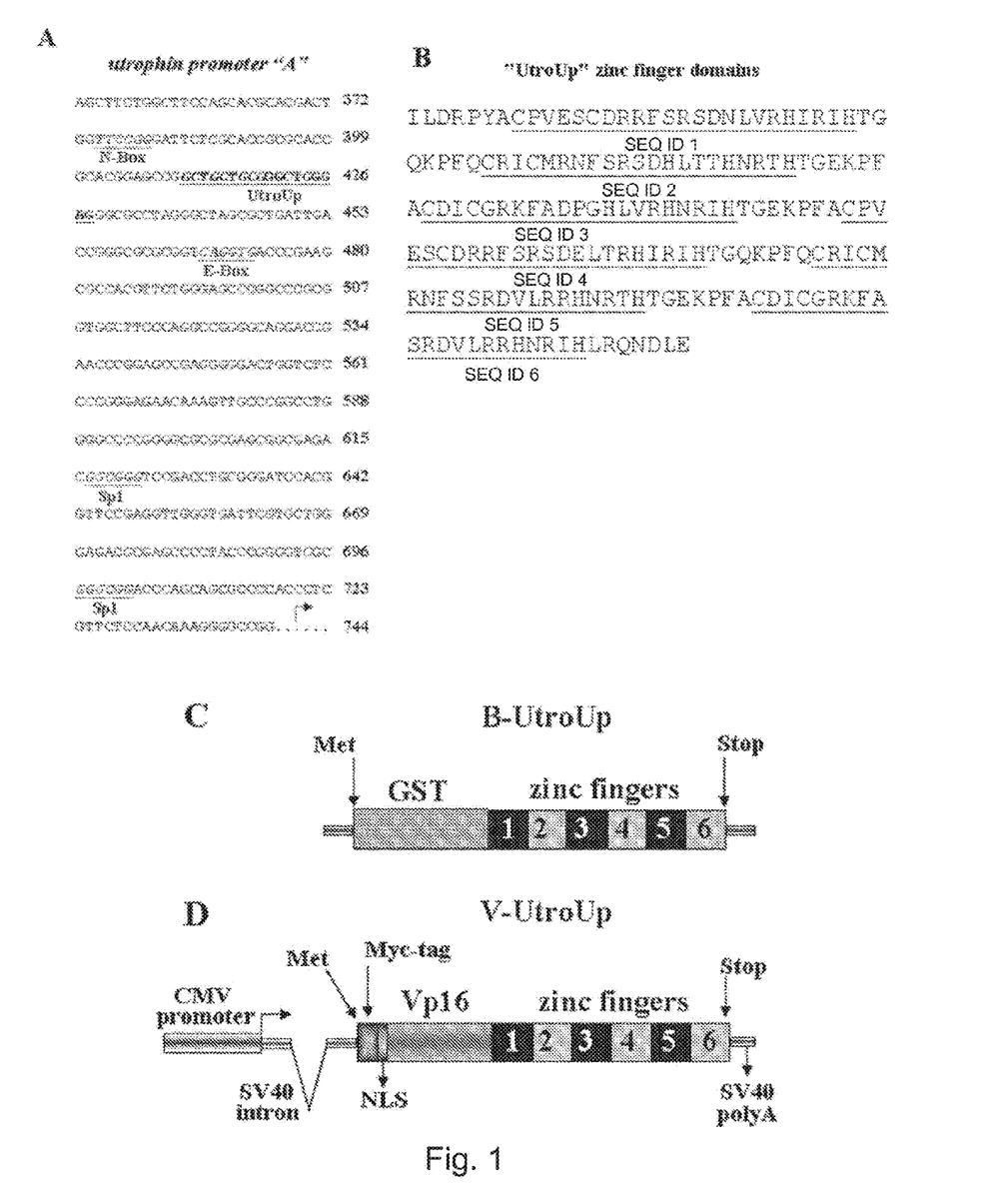
FIG. 1: A) Nucleotidic sequence of the utrophin "A" murine promoter. The DNA target sequence of UtroUp is underlined and in bolt. The bond sites of the main transcriptional factors are indicated. B) Aminoacidic sequence of the domain binding to UtroUp DNA. The sequences of the six zinc finger domains are enumerated and underlined (SEQ ID NO. 1, SEQ ID NO. 2, SEQ ID NO. 3, SEQ ID NO. 4, SEQ ID NO. 5 and SEQ ID NO. 6). C and D) Schemes of the synthetic B-UtroUp constructs for producing and purifying the protein in bacteria and V-UtroUp for assaying the transcriptional properties in mammal cells.

UtroUp comprises six zinc finger domains (Table 1) placed in tandem, and it has been generated with the aim of binding, with very high affinity and specificity, the 18-nucleotide-long DNA target sequence: 5'-GCT GCT GCG GGC TGG GAG-3' (SEQ ID NO. 13), existing both in the human and murine promoter of the "utrophin" gene (FIG. 1A).

TABLE 1

Nucleotidic sequence of the UtroUp domains (SEQ ID NO. 11)

5'TACGCCTGCCCTGTGGAATCTTGCGACCGCCGGTTCTCCCGCAGCGAT

AACCTGGTGCGGCACATCCGGATTCACACCGGCCAGAAACCTTTCCAGTG

CAGGATCTGCATGAGAAATTTCTCCCGGTCCGACCACCTGACCACCCACA

ATAGGACCCACACCGGCGAGAAACCCTTTGCCTGCGACATCTGCGGGAGA

AAGTTCGCCGACCCCGGCCACCTGGTGAGACACAATAGAATCCACACCGG

TGAAAAGCCCTTCGCCTGTCCCGTGGAGAGCTGCGATCGCAGATTCAGCC

GCAGCGACGAGCTGACAAGGCACATCAGAATCCACACCGGGCAGAAGCCT

TABLE 1-continued

Nucleotidic sequence of the UtroUp domains (SEQ ID NO. 11)

TTTCAGTGCCGGATCTGCATGAGGAACTTCAGCTCCCGGGACGTGCTGAG

ACGCCACAATCGCACACACACCGGCGAAAAGCCCTTCGCCTGTGATATTT

GCGGGCGGAAATTTGCCTCCAGAGATGTGCTGCGCCGCCACAACCGCATT

CACCTGAGACAGAACGATCTCGAG 3'

Aminoacidic Sequence of the UtroUp Domains (SEQ ID NO. 12)

ILDRPYACPVESCDRRFSRSDNLVRHIRIHTG

QKPFQCRICMRNFSRSDHLTTHNRTHTGEKPF

ACDICGRKFADPGHLVRHNRIHTGEKPFACPV

ESCDRRFSRSDELTRHIRIHTGQKPFQCRICM

RNFSSRDVLRRHNRTHTGEKPFACDICGRKFA

SRDVLRRHNRIHLRQNDLE

UtroUp has been fused to different protein domains (GST, accession number AAB03573, VP16, accession number P04486) in order to be able to test its biochemical and functional properties.

Two Different Basic Constructs have been Generated:
1) B-UtroUp (Table 2 and 3)

B-UtroUp expresses in bacterial systems (FIG. 1C). It is a fusion protein with the bacterial protein glutathione S-transferase (GST) which allows the expression and purification thereof in quantity sufficient such that its DNA binding properties (specificity and affinity) can be assayed.

TABLE 2

Nucleotidic sequence of B-UtroUp (SEQ ID NO. 7)

5'ATGGCCATCATACGTTATATAGCTGACAAGCACAACATGTTGGGTGGT

TGTCCAAAAGAGCGTGCAGAGATTTCAATGCTTGAAGGAGCGGTTTTGGA

TATTAGATACGGTGTTTCGAGAATTGCATATAGTAAAGACTTTGAAACTC

TCAAAGTTGATTTTCTTAGCAAGCTACCTGAAATGCTGAAAATGTTCGAA

GATCGTTTATGTCATAAAACATATTTAAATGGTGATCATGTAACCCATCC

TGACTTCATGTTGTATGACGCTCTTGATGTTGTTTTATACATGGACCCAA

TGTGCCTGGATGCGTTCCCAAAATTAGTTTGTTTTAAAAAACGTATTGAA

GCTATCCCACAAATTGATAAGTACTTGAAATCCAGCAAGTATATAGCATG

GCCTTTGCAGGGCTGGCAAGCCACGTTTGGTGGTGGCGACCATCCTCCAA

AATCGGATCTGGTTCCGCGTGGATCCCCGGAATTCCCGGGGATCCTGGAT

CGCCCTTACGCCTGCCCTGTGGAATCTTGCGACCGCCGGTTCTCCCGCAG

CGATAACCTGGTGCGGCACATCCGGATTCACACCGGCCAGAAACCTTTCC

AGTGCAGGATCTGCATGAGAAATTTCTCCCGGTCCGACCACCTGACCACC

CACAATAGGACCCACACCGGCGAGAAACCCTTTGCCTGCGACATCTGCGG

GAGAAAGTTCGCCGACCCCGGCCACCTGGTGAGACACAATAGAATCCACA

CCGGTGAAAAGCCCTTCGCCTGTCCCGTGGAGAGCTGCGATCGCAGATTC

TABLE 2-continued

Nucleotidic sequence of B-UtroUp (SEQ ID NO. 7)

AGCCGCAGCGACGAGCTGACAAGGCACATCAGAATCCACACCGGGCAGAA

GCCTTTTCAGTGCCGGATCTGCATGAGGAACTTCAGCTCCCGGGACGTGC

TGAGACGCCACAATCGCACACACACCGGCGAAAAGCCCTTCGCCTGTGAT

ATTTGCGGGCGGAAATTTGCCTCCAGAGATGTGCTGCGCCGCCACAACCG

CATTCACCTGAGACAGAACGATCTCGAGTAA 3'

TABLE 3

Aminoacidic sequence of B-UtroUp (SEQ ID NO. 8)

5'MAIIRYIADKHNMLGGCPKERAEISMLEGAVLDIRYGVSRIAYSKDFE

TLKVDFLSKLPEMLKMFEDRLCHKTYLNGDHVTHPDFMLYDALDVVLYMD

PMCLDAFPKLVCFKKRIEAIPQIDKYLKSSKYIAWPLQGWQATFGGGDHP

PKSDLVPRGSPEFPGILDRPYACPVESCDRRFSRSDNLVRHIRIHTGQKP

FQCRICMRNFSRSDHLTTHNRTHTGEKPFACDICGRKFADPGHLVRHNRI

HTGEKPFACPVESCDRRFSRSDELTRHIRIHTGQKPFQCRICMRNFSSRD

VLRRHNRTHTGEKPFACDICGRKFASRDVLRRHNRIHLRQNDLE 3'

2) V-UtroUp (Table 4 and 5)

V-UtroUp has been constructed for the expression in mammal cells (FIG. 1D) and it has been implemented by synthesizing and assembling various portions described herebelow:
a) The construct includes the region promoting the CMV cytomegalovirus gene (GenBank ADDGENE_VECDB_ 5506 4661, from nucleotide 15 to 591).
b) The transcript V-UtroUp has been equipped with an intron coming from the precocious region of the SV40 virus (from the nucleotide 276 to 621 of the sequence AJ012749). The presence of this intron and the consequent processing thereof increases the stability of the transcript V-UtroUp.
c) In the carboxy-terminal region the following signal has been added (deriving from the SV40 virus), SEQ ID NO. 14:

5'-AACTTGTTTATTGCAGCTTATAATGGTTACAAATAAAGCAATAGCAT

CACAAATTTCACAAATAAAGCATTTTTTTCACTGCATTCTAGTTGTGGTT

TGTCCAAACTCATCAATGTATCTTATCATGTCTGGAT -3' which allows a correct polyadenylation of the transcript.
d) The protein region responsible for binding to DNA is of the zinc-finger type, it is completely synthetic and it comprises six zinc finger domains assembled in tandem and properly modified (FIG. 1B) for recognizing the target sequence: 5'-GCT GCT GCG GGC TGG GAG-3'(SEQ ID NO. 13) present both in the human and murine promoter of the "utrophin" gene.
e) To the zinc-finger region was fused the strong transcription activation domain "Vp16" deriving from the virus herpes simplex (P04486).
In the amino-terminal portion of the V-UtroUp protein two domains have been further added:
f) A nuclear localization signal (NLS, MAPKKKRKV, SEQ ID NO. 15) originating from the Large T precocious protein of the SV40 virus.

g) A sequence of 13 aminoacids (MEQKLISEEDLNE, SEQ ID NO. 16) specifically recognized by the monoclonal antibody 9E10 which allows detecting the protein presence.

TABLE 4

Nucleotidic sequence of V-UtroUp (SEQ ID NO. 9)

5'ATGGAGCAAAAGCTCATTTCTGAAGAGGACTTGAATGAAATGGAGCAA

AAGCTCATTTCTGAAGAGGACTTGAATGAAATGGAGCAAAAGCTCATTTC

TGAAGAGGACTTGAATGAAATGGAGCAAAAGCTCATTTCTGAAGAGGACT

TGAATGAAATGGAGCAAAAGCTCATTTCTGAAGAGGACTTGAATGAAATG

GAGAGCTTGGGCGACCTCACCATGGGCCCTAAAAAGAAGCGTAAAGTCGC

CCCCCCGACCGATGTCAGCCTGGGGGACGAGCTCCACTTAGACGGCGAGG

ACGTGGCGATGGCGCATGCCGACGCGCTAGACGATTTCGATCTGGACATG

TTGGGGGACGGGGATTCCCCGGGTCCGGGATTTACCCCCCACGACTCCGC

CCCCTACGGCGCTCTGGATATGGCCGACTTCGAGTTTGAGCAGATGTTTA

CCGATGCCCTTGGAATTGACGAGTACGGTGGGGAATTCCCGGGGATCCTG

GATCGCCCTTACGCCTGCCCTGTGGAATCTTGCGACCGCCGGTTCTCCCG

CAGCGATAACCTGGTGCGGCACATCCGGATTCACACCGGCCAGAAACCTT

TCCAGTGCAGGATCTGCATGAGAAATTTCTCCCGGTCCGACCACCTGACC

ACCCACAATAGGACCCACACCGGCGAGAAACCCTTTGCCTGCGACATCTG

CGGGAGAAAGTTCGCCGACCCCGGCCACCTGGTGAGACACAATAGAATCC

ACACCGGTGAAAAGCCCTTCGCCTGTCCCGTGGAGAGCTGCGATCGCAGA

TTCAGCCGCAGCGACGAGCTGACAAGGCACATCAGAATCCACACCGGGCA

GAAGCCTTTTCAGTGCCGGATCTGCATGAGGAACTTCAGCTCCCGGGACG

TGCTGAGACGCCACAATCGCACACACACCGGCGAAAAGCCCTTCGCCTGT

GATATTTGCGGGCGGAAATTTGCCTCCAGAGATGTGCTGCGCCGCCACAA

CCGCATTCACCTGAGACAGAACGATCTCGAGTAA 3'

TABLE 5

Aminoacidic sequence of V-UtroUp (SEQ ID NO. 10)

5'MEQKLISEEDLNEMEQKLISEEDLNEMEQKLISEEDLNEMEQKLISEE

DLNEMEQKLISEEDLNEMESLGDLTMGPKKKRKVAPPTDVSLGDELHLDG

EDVAMAHADALDDFDLDMLGDGDSPGPGFTPHDSAPYGALDMADFEFEQM

FTDALGIDEYGGEFEGILDRPYACPVESCDRRFSRSDNLVRHIRIHTGQK

PFQCRICMRNFSRSDHLTTHNRTHTGEKPFACDICGRKFADPGHLVRHNR

IHTGEKPFACPVESCDRRFSRSDELTRHIRIHTGQKPFQCRICMRNFSSR

DVLRRHNRTHTGEKPFACDICGRKFASRDVLRRHNRIHLRQNDLE 3'

Construction of B and V-UtroUp
Construction of B-UtroUp
The synthetic gene B-UtroUp (Table 2) has been cloned in the bacterial expression vector pGEX-4T1 (Pharmacia) in the carboxy-terminal position with respect to the bacterial glutathione S-transferase (GST) protein.
Construction of V-UtroUp
The synthetic gene UtroUp fused to the domain of strong activation of the "Vp16" transcription originating from the virus herpes simplex has been cloned in the eucariotic expression vector pRKS (Clonthec) under the control of the sequences regulating the cytomegalovirus (CMV). The final construct apart from epitope myc (in five copies), has a nuclear localization signal, an intron and a polyadenylation signal, all elements deriving from the SV40 virus (Table 4).

Expression in Bacteria or Mammal Cells

B-UtroUp was expressed in the bacterial strain BL21 (strain of *E. Coli* without protease (Invitrogen) and purified with resin glutathione Sepharose 4B (Pharmacia).

The expression of the V-UtroUp transgene was controlled by using the monoclonal antibody anti myc 9E10 (Calbiochem) in experiments of Western Blot, performed with total and nuclear extracts deriving from HeLa cells transfected transiently. Assays of luciferase activity have been performed on cell extracts deriving from experiments of transient transfection in HeLa cells. The luciferase activity has been measured at the luminometer, model Berthold LB9506.

Experiments of Electrophoretic Delay (EMSA)

In order to measure the dissociation constant (Kd) of B-UtroUp for the DNA target thereof (GCT GCT GCG GGC TGG GAG, SEQ ID No. 13) experiments of electrophoretic delay (EMSA) were performed. In the EMSA assay increasing quantities of B-UtroUp (concentrations from 1 to 120 nM), were placed to incubate with a fixed quantity (10000 cpm equal to about 0.5 ng) of the labelled oligonucleotide (double strand) containing 1 copy of the DNA target. After incubation, the reaction mix was loaded onto an acrylamide gel under non-denaturing conditions. The radioactive gel image was acquired with PhospholMager (Molecular Dinamics) and the band intensity was measured at the different protein concentrations with the ImageQuant programme. The data were analyzed with the KaleidaGraph (Abelbeck Sofware) programme, by assuming as Kd value the protein concentration expressed in nM subtracted of 50% of the radioactive signal.

Results

The authors have designed, synthesized and assayed the biochemical properties a new zinc-finger-based DNA binding domain called "UtroUp" (FIG. 1B).

Binding to DNA Target

Figure 2:
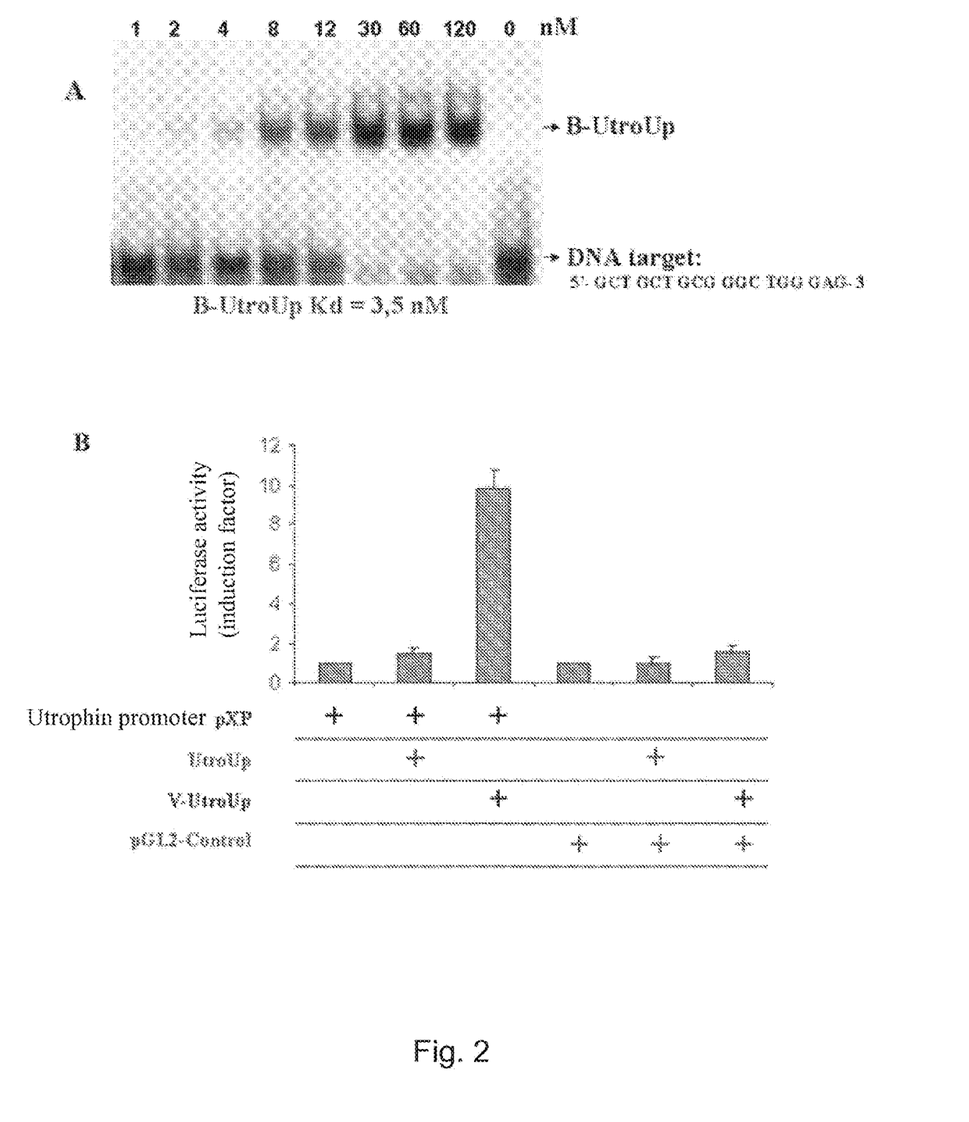
FIG. 2: A) Assay of electrophoretic mobility for determining the dissociation constant (Kd) of the B-UtroUp protein/DNA target complex. The protein concentrations expressed in nanomoles from the first to the ninth lanes are: 1, 2, 4, 8, 12, 30, 60, 120, 0.

The capability of B-UtroUp to bind DNA has been evaluated by means of electrophoretic delay experiments (EMSA), which have allowed calculating the dissociation constant thereof (Kd)) (FIG. 2A). The dissociation constant of B-UtroUp results to be equal to 3.5 nM. This value shows an optimum level of affinity/specificity of B-UtroUp with respect to the DNA target thereof. The dissociation constant of B-UtroUp is comparable to the values obtained for other zinc finger natural proteins and it is significantly lower (more similar) than the Kds determined for other zinc finger synthetic proteins produced by the authors (Corbi et al. 2000, Corbi et al. 2004, Libri et al. 2004).

Electrophoretic delay experiments performed with other properly mutagenized 18-bp sequence, similar to the DNA target sequence of UtroUP, show a strong decrease/absence of binding by UtropUp, confirming the high specificity thereof for binding to the DNA target.

It is important noting that UtroUp, comprising six zinc finger domains (three thereof deriving from Vp16-Jazz (nucleotidic sequence of Jazz: AJ243577, aminoacidic sequence of Jazz: CAB52142, Corbi et al. 2000), shows an affinity of about ten times higher than Vp16-Jazz containing only zinc finger domains (patent application RM 2005 A 000493 of 30 Sep. 2005) (Corbi et al. 2000). The affinity to DNA increases proportionally upon increasing the number of zinc finger domains and upon increasing the number of DNA/protein contacts (Beltran et al. 2006, Onori et al. 2007).

Transcription

The capability of the protein V-UtroUp (FIG. 1D) to modulate the transcription of the luciferase reporter gene under the control of the utrophin promoter, which includes the DNA target sequence of UtroUp (pXP) was verified.

In the histogram shown in FIG. 2B, V-UtroUp displays a high capability of activating the transcription.

BIBLIOGRAPHY

Beltran A et al., 2006. *ASSAY and Drug Dev Technol* 4: 317-331
Bogdanovich S et al., 2004. *J Mol Med.* 82(2):102-15
Corbi N et al., 2000. *Gene Ther* 7:1076-83
Corbi N et al., 2004. *Biochem Cell Biol* 82(4):428-36
Davies K E et al., 1983. *Nucleic Acids Res* April 25; 11(8): 2303-12
Khurana T S, Davies K E. 2003. *Nat. Rev. Drug Discov.* 2:379-90
Libri V, et al., 2004. *FEBS Lett.* 560 (1-3): 75-80
Love D R et al., 1989. *Nature.* May 4; 339(6219):55-8
Maffei E, et al., 2007. *PLoS ONE* 22; 2(1):e774
Matsumura K et al., 1992. *Nature* 10; 360(6404):588-91
Miura P, Jasmin B J. 2006. *Trends Mol Med.* 3:122-9
Onori A et al., 2007. *Biochem Cell Biol,* (3)358-365
Rafael J A et al., 1998. *Nat. Genet.* 19:79-82
Tinsley J M et al., 1996. *Nature* 384:349-53
Voisin V, de la Porte S.2004. Therapeutic *Int Rev Cytol.* 240: 1-30

The invention claimed is:

1. A synthetic protein having at six zinc finger domains and that modulates utrophin gene transcription by binding to a nucleotidic sequence comprised in a utrophin gene untranscribed regulatory sequence and
wherein the six zinc finger domains are SEQ ID NO: 1, SEQ ID NO: 2, SEQ ID NO: 3, SEQ ID NO: 4, SEQ ID NO: 5 and SEQ ID NO: 6.

2. The synthetic protein according to claim 1 which binds to the nucleotidic sequence consisting of the sequence: GCT GCT GCG GGC TGG GAG (SEQ ID NO 13).

3. The synthetic protein according to claim 1 consisting of SEQ ID NO: 12.

4. The synthetic protein according to claim 1 consisting of SEQ ID NO: 8 or SEQ ID NO: 10.

5. A synthetic nucleic acid molecule comprising a nucleotide sequence codifying for a protein having six zinc finger domains and that modulates utrophin gene transcription by binding to a nucleotidic sequence comprised in a utrophin gene untranscribed regulatory sequence and wherein the six zinc finger domains are SEQ ID NO: 1, SEQ ID NO: 2, SEQ ID NO: 3, SEQ ID NO: 4, SEQ ID NO: 5 and SEQ ID NO: 6.

6. The synthetic nucleic acid molecule according to claim 5 codifying for a protein comprising SEQ ID NO: 12.

7. The synthetic nucleic acid molecule according to claim 5 codifying for a protein consisting of SEQ ID NO: 12.

8. The synthetic nucleic acid molecule according to claim 7 consisting of SEQ ID NO: 11.

9. The synthetic nucleic acid molecule according to claim 5 codifying for a protein consisting of SEQ ID NO: 8 or SEQ ID NO 10.

10. The synthetic nucleic acid molecule according to claim 9 consisting of SEQ ID NO: 7 or SEQ ID NO: 9, respectively.

11. An expression vector comprising the synthetic nucleic acid molecule according to claim 5.

12. A recombinant host cell comprising the vector according to claim 11.

13. A method of treating muscular pathology, comprising administering the synthetic protein according to claim 1 to a patient in need thereof.

14. The method according to claim 13 wherein the muscular pathology is Duchenne (DMD) or Becker (BMD) muscular dystrophy.

* * * * *

SEQUENCE LISTING

<160> NUMBER OF SEQ ID NOS: 16

<210> SEQ ID NO 1
<211> LENGTH: 23
<212> TYPE: PRT
<213> ORGANISM: Artificial
<220> FEATURE:
<223> OTHER INFORMATION: zinc finger domain

<400> SEQUENCE: 1

Cys Pro Val Glu Ser Cys Asp Arg Arg Phe Ser Arg Ser Asp Asn Leu
1               5                   10                  15

Val Arg His Ile Arg Ile His

20

<210> SEQ ID NO 2
<211> LENGTH: 21
<212> TYPE: PRT
<213> ORGANISM: Artificial
<220> FEATURE:
<223> OTHER INFORMATION: zinc finger domain

<400> SEQUENCE: 2

Cys Arg Ile Cys Met Arg Asn Phe Ser Arg Ser Asp His Leu Thr Thr
1               5                   10                  15

His Asn Arg Thr His
            20

<210> SEQ ID NO 3
<211> LENGTH: 21
<212> TYPE: PRT
<213> ORGANISM: Artificial
<220> FEATURE:
<223> OTHER INFORMATION: zinc finger domain

<400> SEQUENCE: 3

Cys Asp Ile Cys Gly Arg Lys Phe Ala Asp Pro Gly His Leu Val Arg
1               5                   10                  15

His Asn Arg Ile His
            20

<210> SEQ ID NO 4
<211> LENGTH: 23
<212> TYPE: PRT
<213> ORGANISM: Artificial
<220> FEATURE:
<223> OTHER INFORMATION: zinc finger domain

<400> SEQUENCE: 4

Cys Pro Val Glu Ser Cys Asp Arg Arg Phe Ser Arg Ser Asp Glu Leu
1               5                   10                  15

Thr Arg His Ile Arg Ile His
            20

<210> SEQ ID NO 5
<211> LENGTH: 21
<212> TYPE: PRT
<213> ORGANISM: Artificial
<220> FEATURE:
<223> OTHER INFORMATION: zinc finger domain

<400> SEQUENCE: 5

Cys Arg Ile Cys Met Arg Asn Phe Ser Ser Arg Asp Val Leu Arg Arg
1               5                   10                  15

His Asn Arg Thr His
            20

<210> SEQ ID NO 6
<211> LENGTH: 21
<212> TYPE: PRT
<213> ORGANISM: Artificial
<220> FEATURE:
<223> OTHER INFORMATION: zinc finger domain

<400> SEQUENCE: 6

Cys Asp Ile Cys Gly Arg Lys Phe Ala Ser Arg Asp Val Leu Arg Arg
1               5                   10                  15

His Asn Arg Ile His

-continued

<210> SEQ ID NO 7
<211> LENGTH: 1029
<212> TYPE: DNA
<213> ORGANISM: Artificial
<220> FEATURE:
<223> OTHER INFORMATION: B-Utrop
<220> FEATURE:
<221> NAME/KEY: CDS
<222> LOCATION: (1)..(1029)

<400> SEQUENCE: 7

```
atg gcc atc ata cgt tat ata gct gac aag cac aac atg ttg ggt ggt      48
Met Ala Ile Ile Arg Tyr Ile Ala Asp Lys His Asn Met Leu Gly Gly
1               5                   10                  15 tgt cca aaa gag cgt gca gag att tca atg ctt gaa gga gcg gtt ttg      96
Cys Pro Lys Glu Arg Ala Glu Ile Ser Met Leu Glu Gly Ala Val Leu
            20                  25                  30 gat att aga tac ggt gtt tcg aga att gca tat agt aaa gac ttt gaa     144
Asp Ile Arg Tyr Gly Val Ser Arg Ile Ala Tyr Ser Lys Asp Phe Glu
        35                  40                  45 act ctc aaa gtt gat ttt ctt agc aag cta cct gaa atg ctg aaa atg     192
Thr Leu Lys Val Asp Phe Leu Ser Lys Leu Pro Glu Met Leu Lys Met
    50                  55                  60 ttc gaa gat cgt tta tgt cat aaa aca tat tta aat ggt gat cat gta     240
Phe Glu Asp Arg Leu Cys His Lys Thr Tyr Leu Asn Gly Asp His Val
65                  70                  75                  80 acc cat cct gac ttc atg ttg tat gac gct ctt gat gtt gtt tta tac     288
Thr His Pro Asp Phe Met Leu Tyr Asp Ala Leu Asp Val Val Leu Tyr
                85                  90                  95 atg gac cca atg tgc ctg gat gcg ttc cca aaa tta gtt tgt ttt aaa     336
Met Asp Pro Met Cys Leu Asp Ala Phe Pro Lys Leu Val Cys Phe Lys
            100                 105                 110 aaa cgt att gaa gct atc cca caa att gat aag tac ttg aaa tcc agc     384
Lys Arg Ile Glu Ala Ile Pro Gln Ile Asp Lys Tyr Leu Lys Ser Ser
        115                 120                 125 aag tat ata gca tgg cct ttg cag ggc tgg caa gcc acg ttt ggt ggt     432
Lys Tyr Ile Ala Trp Pro Leu Gln Gly Trp Gln Ala Thr Phe Gly Gly
    130                 135                 140 ggc gac cat cct cca aaa tcg gat ctg gtt ccg cgt gga tcc ccg gaa     480
Gly Asp His Pro Pro Lys Ser Asp Leu Val Pro Arg Gly Ser Pro Glu
145                 150                 155                 160 ttc ccg ggg atc ctg gat cgc cct tac gcc tgc cct gtg gaa tct tgc     528
Phe Pro Gly Ile Leu Asp Arg Pro Tyr Ala Cys Pro Val Glu Ser Cys
                165                 170                 175 gac cgc cgg ttc tcc cgc agc gat aac ctg gtg cgg cac atc cgg att     576
Asp Arg Arg Phe Ser Arg Ser Asp Asn Leu Val Arg His Ile Arg Ile
            180                 185                 190 cac acc ggc cag aaa cct ttc cag tgc agg atc tgc atg aga aat ttc     624
His Thr Gly Gln Lys Pro Phe Gln Cys Arg Ile Cys Met Arg Asn Phe
        195                 200                 205 tcc cgg tcc gac cac ctg acc acc cac aat agg acc cac acc ggc gag     672
Ser Arg Ser Asp His Leu Thr Thr His Asn Arg Thr His Thr Gly Glu
    210                 215                 220 aaa ccc ttt gcc tgc gac atc tgc ggg aga aag ttc gcc gac ccc ggc     720
Lys Pro Phe Ala Cys Asp Ile Cys Gly Arg Lys Phe Ala Asp Pro Gly
225                 230                 235                 240 cac ctg gtg aga cac aat aga atc cac acc ggt gaa aag ccc ttc gcc     768
His Leu Val Arg His Asn Arg Ile His Thr Gly Glu Lys Pro Phe Ala
                245                 250                 255 tgt ccc gtg gag agc tgc gat cgc aga ttc agc cgc agc gac gag ctg     816
Cys Pro Val Glu Ser Cys Asp Arg Arg Phe Ser Arg Ser Asp Glu Leu
```

|   |   |   |   |   |   |   |   |   |   |   |   |   |   |   |   |      |
|---|---|---|---|---|---|---|---|---|---|---|---|---|---|---|---|------|
| Cys | Pro | Val | Glu | Ser | Cys | Asp | Arg | Arg | Phe | Ser | Arg | Ser | Asp | Glu | Leu | |
|   |   |   | 260 |   |   |   | 265 |   |   |   | 270 |   |   |   |   | |

| aca | agg | cac | atc | aga | atc | cac | acc | ggg | cag | aag | cct | ttt | cag | tgc | cgg | 864 |
|-----|-----|-----|-----|-----|-----|-----|-----|-----|-----|-----|-----|-----|-----|-----|-----|-----|
| Thr | Arg | His | Ile | Arg | Ile | His | Thr | Gly | Gln | Lys | Pro | Phe | Gln | Cys | Arg |     |
|     |     | 275 |     |     |     | 280 |     |     |     | 285 |     |     |     |     |     |     |

| atc | tgc | atg | agg | aac | ttc | agc | tcc | cgg | gac | gtg | ctg | aga | cgc | cac | aat | 912 |
|-----|-----|-----|-----|-----|-----|-----|-----|-----|-----|-----|-----|-----|-----|-----|-----|-----|
| Ile | Cys | Met | Arg | Asn | Phe | Ser | Ser | Arg | Asp | Val | Leu | Arg | Arg | His | Asn |     |
|     |     | 290 |     |     |     | 295 |     |     |     | 300 |     |     |     |     |     |     |

| cgc | aca | cac | acc | ggc | gaa | aag | ccc | ttc | gcc | tgt | gat | att | tgc | ggg | cgg | 960 |
|-----|-----|-----|-----|-----|-----|-----|-----|-----|-----|-----|-----|-----|-----|-----|-----|-----|
| Arg | Thr | His | Thr | Gly | Glu | Lys | Pro | Phe | Ala | Cys | Asp | Ile | Cys | Gly | Arg |     |
| 305 |     |     |     | 310 |     |     |     | 315 |     |     |     | 320 |     |     |     |     |

| aaa | ttt | gcc | tcc | aga | gat | gtg | ctg | cgc | cgc | cac | aac | cgc | att | cac | ctg | 1008 |
|-----|-----|-----|-----|-----|-----|-----|-----|-----|-----|-----|-----|-----|-----|-----|-----|------|
| Lys | Phe | Ala | Ser | Arg | Asp | Val | Leu | Arg | Arg | His | Asn | Arg | Ile | His | Leu |      |
|     |     |     |     | 325 |     |     |     | 330 |     |     |     | 335 |     |     |     |      |

| aga | cag | aac | gat | ctc | gag | taa | | | | | | | | | | 1029 |
|-----|-----|-----|-----|-----|-----|-----|---|---|---|---|---|---|---|---|---|------|
| Arg | Gln | Asn | Asp | Leu | Glu |     | | | | | | | | | |      |
|     |     |     | 340 |     |     |     | | | | | | | | | |      |

```
<210> SEQ ID NO 8
<211> LENGTH: 342
<212> TYPE: PRT
<213> ORGANISM: Artificial
<220> FEATURE:
<223> OTHER INFORMATION: Synthetic Construct

<400> SEQUENCE: 8
```

Met Ala Ile Ile Arg Tyr Ile Ala Asp Lys His Asn Met Leu Gly Gly
1               5                   10                  15

Cys Pro Lys Glu Arg Ala Glu Ile Ser Met Leu Glu Gly Ala Val Leu
                20                  25                  30

Asp Ile Arg Tyr Gly Val Ser Arg Ile Ala Tyr Ser Lys Asp Phe Glu
            35                  40                  45

Thr Leu Lys Val Asp Phe Leu Ser Lys Leu Pro Glu Met Leu Lys Met
        50                  55                  60

Phe Glu Asp Arg Leu Cys His Lys Thr Tyr Leu Asn Gly Asp His Val
65                  70                  75                  80

Thr His Pro Asp Phe Met Leu Tyr Asp Ala Leu Asp Val Val Leu Tyr
                85                  90                  95

Met Asp Pro Met Cys Leu Asp Ala Phe Pro Lys Leu Val Cys Phe Lys
            100                 105                 110

Lys Arg Ile Glu Ala Ile Pro Gln Ile Asp Lys Tyr Leu Lys Ser Ser
        115                 120                 125

Lys Tyr Ile Ala Trp Pro Leu Gln Gly Trp Gln Ala Thr Phe Gly Gly
130                 135                 140

Gly Asp His Pro Pro Lys Ser Asp Leu Val Pro Arg Gly Ser Pro Glu
145                 150                 155                 160

Phe Pro Gly Ile Leu Asp Arg Pro Tyr Ala Cys Pro Val Glu Ser Cys
                165                 170                 175

Asp Arg Arg Phe Ser Arg Ser Asp Asn Leu Val Arg His Ile Arg Ile
            180                 185                 190

His Thr Gly Gln Lys Pro Phe Gln Cys Arg Ile Cys Met Arg Asn Phe
        195                 200                 205

Ser Arg Ser Asp His Leu Thr Thr His Asn Arg Thr His Thr Gly Glu
210                 215                 220

Lys Pro Phe Ala Cys Asp Ile Cys Gly Arg Lys Phe Ala Asp Pro Gly
225                 230                 235                 240

His Leu Val Arg His Asn Arg Ile His Thr Gly Glu Lys Pro Phe Ala
                245                 250                 255

```
            Cys Pro Val Glu Ser Cys Asp Arg Arg Phe Ser Arg Ser Asp Glu Leu
                        260                 265                 270

Thr Arg His Ile Arg Ile His Thr Gly Gln Lys Pro Phe Gln Cys Arg
                    275                 280                 285

Ile Cys Met Arg Asn Phe Ser Arg Asp Val Leu Arg Arg His Asn
                290                 295                 300

Arg Thr His Thr Gly Glu Lys Pro Phe Ala Cys Asp Ile Cys Gly Arg
            305                 310                 315                 320

Lys Phe Ala Ser Arg Asp Val Leu Arg His Asn Arg Ile His Leu
                            325                 330                 335

Arg Gln Asn Asp Leu Glu
                            340

<210> SEQ ID NO 9
<211> LENGTH: 1032
<212> TYPE: DNA
<213> ORGANISM: Artificial
<220> FEATURE:
<223> OTHER INFORMATION: V-Utrop
<220> FEATURE:
<221> NAME/KEY: CDS
<222> LOCATION: (1)..(1032)

<400> SEQUENCE: 9 atg gag caa aag ctc att tct gaa gag gac ttg aat gaa atg gag caa        48
Met Glu Gln Lys Leu Ile Ser Glu Glu Asp Leu Asn Glu Met Glu Gln
1               5                   10                  15 aag ctc att tct gaa gag gac ttg aat gaa atg gag caa aag ctc att        96
Lys Leu Ile Ser Glu Glu Asp Leu Asn Glu Met Glu Gln Lys Leu Ile
            20                  25                  30 tct gaa gag gac ttg aat gaa atg gag caa aag ctc att tct gaa gag       144
Ser Glu Glu Asp Leu Asn Glu Met Glu Gln Lys Leu Ile Ser Glu Glu
        35                  40                  45 gac ttg aat gaa atg gag caa aag ctc att tct gaa gag gac ttg aat       192
Asp Leu Asn Glu Met Glu Gln Lys Leu Ile Ser Glu Glu Asp Leu Asn
    50                  55                  60 gaa atg gag agc ttg ggc gac ctc acc atg ggc cct aaa aag aag cgt       240
Glu Met Glu Ser Leu Gly Asp Leu Thr Met Gly Pro Lys Lys Lys Arg
65                  70                  75                  80 aaa gtc gcc ccc ccg acc gat gtc agc ctg ggg gac gag ctc cac tta       288
Lys Val Ala Pro Pro Thr Asp Val Ser Leu Gly Asp Glu Leu His Leu
                85                  90                  95 gac ggc gag gac gtg gcg atg gcg cat gcc gac gcg cta gac gat ttc       336
Asp Gly Glu Asp Val Ala Met Ala His Ala Asp Ala Leu Asp Asp Phe
            100                 105                 110 gat ctg gac atg ttg ggg gac ggg gat tcc ccg ggt ccg gga ttt acc       384
Asp Leu Asp Met Leu Gly Asp Gly Asp Ser Pro Gly Pro Gly Phe Thr
        115                 120                 125 ccc cac gac tcc gcc ccc tac ggc gct ctg gat atg gcc gac ttc gag       432
Pro His Asp Ser Ala Pro Tyr Gly Ala Leu Asp Met Ala Asp Phe Glu
    130                 135                 140 ttt gag cag atg ttt acc gat gcc ctt gga att gac gag tac ggt ggg       480
Phe Glu Gln Met Phe Thr Asp Ala Leu Gly Ile Asp Glu Tyr Gly Gly
145                 150                 155                 160 gaa ttc ccg ggg atc ctg gat cgc cct tac gcc tgc cct gtg gaa tct       528
Glu Phe Pro Gly Ile Leu Asp Arg Pro Tyr Ala Cys Pro Val Glu Ser
                165                 170                 175 tgc gac cgc cgg ttc tcc cgc agc gat aac ctg gtg cgg cac atc cgg       576
Cys Asp Arg Arg Phe Ser Arg Ser Asp Asn Leu Val Arg His Ile Arg
            180                 185                 190
```

```
att cac acc ggc cag aaa cct ttc cag tgc agg atc tgc atg aga aat    624
Ile His Thr Gly Gln Lys Pro Phe Gln Cys Arg Ile Cys Met Arg Asn
        195                 200                 205 ttc tcc cgg tcc gac cac ctg acc acc cac aat agg acc cac acc ggc    672
Phe Ser Arg Ser Asp His Leu Thr Thr His Asn Arg Thr His Thr Gly
210                 215                 220 gag aaa ccc ttt gcc tgc gac atc tgc ggg aga aag ttc gcc gac ccc    720
Glu Lys Pro Phe Ala Cys Asp Ile Cys Gly Arg Lys Phe Ala Asp Pro
225                 230                 235                 240 ggc cac ctg gtg aga cac aat aga atc cac acc ggt gaa aag ccc ttc    768
Gly His Leu Val Arg His Asn Arg Ile His Thr Gly Glu Lys Pro Phe
                245                 250                 255 gcc tgt ccc gtg gag agc tgc gat cgc aga ttc agc cgc agc gac gag    816
Ala Cys Pro Val Glu Ser Cys Asp Arg Arg Phe Ser Arg Ser Asp Glu
            260                 265                 270 ctg aca agg cac atc aga atc cac acc ggg cag aag cct ttt cag tgc    864
Leu Thr Arg His Ile Arg Ile His Thr Gly Gln Lys Pro Phe Gln Cys
        275                 280                 285 cgg atc tgc atg agg aac ttc agc tcc cgg gac gtg ctg aga cgc cac    912
Arg Ile Cys Met Arg Asn Phe Ser Ser Arg Asp Val Leu Arg Arg His
290                 295                 300 aat cgc aca cac acc ggc gaa aag ccc ttc gcc tgt gat att tgc ggg    960
Asn Arg Thr His Thr Gly Glu Lys Pro Phe Ala Cys Asp Ile Cys Gly
305                 310                 315                 320 cgg aaa ttt gcc tcc aga gat gtg ctg cgc cgc cac aac cgc att cac   1008
Arg Lys Phe Ala Ser Arg Asp Val Leu Arg Arg His Asn Arg Ile His
                325                 330                 335 ctg aga cag aac gat ctc gag taa                                    1032
Leu Arg Gln Asn Asp Leu Glu
            340

<210> SEQ ID NO 10
<211> LENGTH: 343
<212> TYPE: PRT
<213> ORGANISM: Artificial
<220> FEATURE:
<223> OTHER INFORMATION: Synthetic Construct

<400> SEQUENCE: 10

Met Glu Gln Lys Leu Ile Ser Glu Glu Asp Leu Asn Glu Met Glu Gln
1               5                   10                  15

Lys Leu Ile Ser Glu Glu Asp Leu Asn Met Glu Gln Lys Leu Ile
            20                  25                  30

Ser Glu Glu Asp Leu Asn Glu Met Glu Gln Lys Leu Ile Ser Glu Glu
        35                  40                  45

Asp Leu Asn Glu Met Glu Gln Lys Leu Ile Ser Glu Glu Asp Leu Asn
    50                  55                  60

Glu Met Glu Ser Leu Gly Asp Leu Thr Met Gly Pro Lys Lys Lys Arg
65                  70                  75                  80

Lys Val Ala Pro Pro Thr Asp Val Ser Leu Gly Asp Glu Leu His Leu
                85                  90                  95

Asp Gly Glu Asp Val Ala Met Ala His Ala Asp Ala Leu Asp Asp Phe
            100                 105                 110

Asp Leu Asp Met Leu Gly Asp Gly Asp Ser Pro Gly Pro Gly Phe Thr
        115                 120                 125

Pro His Asp Ser Ala Pro Tyr Gly Ala Leu Asp Met Ala Asp Phe Glu
    130                 135                 140

Phe Glu Gln Met Phe Thr Asp Ala Leu Gly Ile Asp Glu Tyr Gly Gly
145                 150                 155                 160
```

```
Glu Phe Pro Gly Ile Leu Asp Arg Pro Tyr Ala Cys Pro Val Glu Ser
                165                 170                 175

Cys Asp Arg Arg Phe Ser Arg Ser Asp Asn Leu Val Arg His Ile Arg
            180                 185                 190

Ile His Thr Gly Gln Lys Pro Phe Gln Cys Arg Ile Cys Met Arg Asn
        195                 200                 205

Phe Ser Arg Ser Asp His Leu Thr Thr His Asn Arg Thr His Thr Gly
    210                 215                 220

Glu Lys Pro Phe Ala Cys Asp Ile Cys Gly Arg Lys Phe Ala Asp Pro
225                 230                 235                 240

Gly His Leu Val Arg His Asn Arg Ile His Thr Gly Glu Lys Pro Phe
                245                 250                 255

Ala Cys Pro Val Glu Ser Cys Asp Arg Arg Phe Ser Arg Ser Asp Glu
            260                 265                 270

Leu Thr Arg His Ile Arg Ile His Thr Gly Gln Lys Pro Phe Gln Cys
        275                 280                 285

Arg Ile Cys Met Arg Asn Phe Ser Arg Ser Asp Val Leu Arg Arg His
    290                 295                 300

Asn Arg Thr His Thr Gly Glu Lys Pro Phe Ala Cys Asp Ile Cys Gly
305                 310                 315                 320

Arg Lys Phe Ala Ser Arg Asp Val Leu Arg Arg His Asn Arg Ile His
                325                 330                 335

Leu Arg Gln Asn Asp Leu Glu
            340

<210> SEQ ID NO 11
<211> LENGTH: 522
<212> TYPE: DNA
<213> ORGANISM: Artificial
<220> FEATURE:
<223> OTHER INFORMATION: UtroUp domains
<220> FEATURE:
<221> NAME/KEY: CDS
<222> LOCATION: (1)..(522)

<400> SEQUENCE: 11 tac gcc tgc cct gtg gaa tct tgc gac cgc cgg ttc tcc cgc agc gat    48
Tyr Ala Cys Pro Val Glu Ser Cys Asp Arg Arg Phe Ser Arg Ser Asp
1               5                   10                  15 aac ctg gtg cgg cac atc cgg att cac acc ggc cag aaa cct ttc cag    96
Asn Leu Val Arg His Ile Arg Ile His Thr Gly Gln Lys Pro Phe Gln
            20                  25                  30 tgc agg atc tgc atg aga aat ttc tcc cgg tcc gac cac ctg acc acc   144
Cys Arg Ile Cys Met Arg Asn Phe Ser Arg Ser Asp His Leu Thr Thr
        35                  40                  45 cac aat agg acc cac acc ggc gag aaa ccc ttt gcc tgc gac atc tgc   192
His Asn Arg Thr His Thr Gly Glu Lys Pro Phe Ala Cys Asp Ile Cys
    50                  55                  60 ggg aga aag ttc gcc gac ccc ggc cac ctg gtg aga cac aat aga atc   240
Gly Arg Lys Phe Ala Asp Pro Gly His Leu Val Arg His Asn Arg Ile
65                  70                  75                  80 cac acc ggt gaa aag ccc ttc gcc tgt ccc gtg gag agc tgc gat cgc   288
His Thr Gly Glu Lys Pro Phe Ala Cys Pro Val Glu Ser Cys Asp Arg
                85                  90                  95 aga ttc agc cgc agc gac gag ctg aca agg cac atc aga atc cac acc   336
Arg Phe Ser Arg Ser Asp Glu Leu Thr Arg His Ile Arg Ile His Thr
            100                 105                 110 ggg cag aag cct ttt cag tgc cgg atc tgc atg agg aac ttc agc tcc   384
Gly Gln Lys Pro Phe Gln Cys Arg Ile Cys Met Arg Asn Phe Ser Ser
        115                 120                 125
```

```
cgg gac gtg ctg aga cgc cac aat cgc aca cac acc ggc gaa aag ccc       432
Arg Asp Val Leu Arg Arg His Asn Arg Thr His Thr Gly Glu Lys Pro
        130                 135                 140 ttc gcc tgt gat att tgc ggg cgg aaa ttt gcc tcc aga gat gtg ctg       480
Phe Ala Cys Asp Ile Cys Gly Arg Lys Phe Ala Ser Arg Asp Val Leu
145                 150                 155                 160 cgc cgc cac aac cgc att cac ctg aga cag aac gat ctc gag               522
Arg Arg His Asn Arg Ile His Leu Arg Gln Asn Asp Leu Glu
                165                 170

<210> SEQ ID NO 12
<211> LENGTH: 174
<212> TYPE: PRT
<213> ORGANISM: Artificial
<220> FEATURE:
<223> OTHER INFORMATION: Synthetic Construct

<400> SEQUENCE: 12

Tyr Ala Cys Pro Val Glu Ser Cys Asp Arg Arg Phe Ser Arg Ser Asp
1               5                   10                  15

Asn Leu Val Arg His Ile Arg Ile His Thr Gly Gln Lys Pro Phe Gln
            20                  25                  30

Cys Arg Ile Cys Met Arg Asn Phe Ser Arg Ser Asp His Leu Thr Thr
        35                  40                  45

His Asn Arg Thr His Thr Gly Glu Lys Pro Phe Ala Cys Asp Ile Cys
    50                  55                  60

Gly Arg Lys Phe Ala Asp Pro Gly His Leu Val Arg His Asn Arg Ile
65                  70                  75                  80

His Thr Gly Glu Lys Pro Phe Ala Cys Pro Val Glu Ser Cys Asp Arg
                85                  90                  95

Arg Phe Ser Arg Ser Asp Glu Leu Thr Arg His Ile Arg Ile His Thr
            100                 105                 110

Gly Gln Lys Pro Phe Gln Cys Arg Ile Cys Met Arg Asn Phe Ser Ser
        115                 120                 125

Arg Asp Val Leu Arg Arg His Asn Arg Thr His Thr Gly Glu Lys Pro
    130                 135                 140

Phe Ala Cys Asp Ile Cys Gly Arg Lys Phe Ala Ser Arg Asp Val Leu
145                 150                 155                 160

Arg Arg His Asn Arg Ile His Leu Arg Gln Asn Asp Leu Glu
                165                 170

<210> SEQ ID NO 13
<211> LENGTH: 18
<212> TYPE: DNA
<213> ORGANISM: Artificial
<220> FEATURE:
<223> OTHER INFORMATION: target sequence

<400> SEQUENCE: 13
gctgctgcgg gctgggag                                                    18

<210> SEQ ID NO 14
<211> LENGTH: 134
<212> TYPE: DNA
<213> ORGANISM: Artificial
<220> FEATURE:
<223> OTHER INFORMATION: signal sequence

<400> SEQUENCE: 14
aacttgttta ttgcagctta taatggttac aaataaagca atagcatcac aaatttcaca    60
```

-continued

```
aataaagcat tttttcact gcattctagt tgtggtttgt ccaaactcat caatgtatct    120
tatcatgtct ggat                                                    134
```

```
<210> SEQ ID NO 15
<211> LENGTH: 9
<212> TYPE: PRT
<213> ORGANISM: Artificial
<220> FEATURE:
<223> OTHER INFORMATION: NLS

<400> SEQUENCE: 15

Met Ala Pro Lys Lys Lys Arg Lys Val
1               5
```

```
<210> SEQ ID NO 16
<211> LENGTH: 13
<212> TYPE: PRT
<213> ORGANISM: Artificial
<220> FEATURE:
<223> OTHER INFORMATION: recognition sequence by antibody 9E10

<400> SEQUENCE: 16

Met Glu Gln Lys Leu Ile Ser Glu Glu Asp Leu Asn Glu
1               5                   10
```